United States Patent
Sugita et al.

(10) Patent No.: US 8,371,289 B2
(45) Date of Patent: Feb. 12, 2013

(54) INHALER

(75) Inventors: Masaru Sugita, Tokyo (JP); Hiroshi Komatsu, Yokohama (JP); Toshiyuki Nobutani, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 837 days.

(21) Appl. No.: 12/509,952

(22) Filed: Jul. 27, 2009

(65) Prior Publication Data

US 2010/0024814 A1 Feb. 4, 2010

(30) Foreign Application Priority Data

Aug. 4, 2008 (JP) ................. 2008-200942

(51) Int. Cl.
*A61M 11/00* (2006.01)
(52) U.S. Cl. .......... 128/200.14; 128/200.24; 128/203.12
(58) Field of Classification Search ............ 128/200.14–200.24, 203.12, 203.15
See application file for complete search history.

(56) References Cited

U.S. PATENT DOCUMENTS

| | | | | | |
|---|---|---|---|---|---|
| 4,520,808 | A | * | 6/1985 | LaBauve ................. | 128/200.14 |
| 5,692,492 | A | | 12/1997 | Bruna et al. ............ | 128/200.23 |
| 6,516,796 | B1 | * | 2/2003 | Cox et al. ................ | 128/200.23 |
| 7,073,499 | B1 | | 7/2006 | Reinhold et al. ........ | 128/200.18 |
| 7,380,550 | B2 | * | 6/2008 | Sexton et al. ........... | 128/200.14 |
| 7,594,507 | B2 | * | 9/2009 | Davis ....................... | 128/200.14 |
| 7,819,115 | B2 | * | 10/2010 | Sexton et al. ........... | 128/200.23 |
| 8,056,556 | B2 | * | 11/2011 | Childers et al. ......... | 128/200.14 |
| 2008/0011292 | A1 | | 1/2008 | Sugita et al. ............. | 128/200.19 |
| 2008/0163869 | A1 | | 7/2008 | Nobutani et al. ........ | 128/200.23 |
| 2008/0190422 | A1 | | 8/2008 | Nobutani et al. ........ | 128/200.24 |
| 2008/0295827 | A1 | | 12/2008 | Kobayashi ............... | 128/200.16 |
| 2009/0260624 | A1 | | 10/2009 | Wada et al. .............. | 128/203.12 |

FOREIGN PATENT DOCUMENTS

| | | |
|---|---|---|
| EP | 28929 | 5/1981 |
| EP | 1847287 | 10/2007 |
| JP | 04-312469 | 11/1992 |
| JP | 2004-283245 | 10/2004 |
| JP | 2004-290593 | 10/2004 |
| JP | 2006-212203 | 8/2006 |
| JP | 2006-280685 A | 10/2006 |
| WO | WO 2006-083014 | 8/2006 |

OTHER PUBLICATIONS

Chinese Office Action dated Jul. 13, 2011, issued in counterpart Chinese Patent Application No. 200910160195.5, and translation.
Japanese Office Action dated Oct. 23, 2012 issued in the counterpart application No. 2008-200942 along with partial English-language translation.

* cited by examiner

*Primary Examiner* — Glenn Richman
(74) *Attorney, Agent, or Firm* — Fitzpatrick, Cella, Harper & Scinto (57) ABSTRACT

An inhaler includes a medicine cartridge having at least an ejection head and a first electrical connection section for supplying the ejection head with electric power necessary for ejecting medicine, an inhaler body having a medicine cartridge mounting section and an inhalation piece. The inhaler is so constructed that an electric circuit for supplying the ejection head with electric power necessary for ejecting medicine by way of the first electrical connection section is made operable by mounting and rigidly securing the inhalation piece onto the inhaler body. The inhaler can be operated by a user with ease and the ejection head is reliably electrically energized only when the inhaler is operated.

7 Claims, 9 Drawing Sheets

INHALER

BACKGROUND OF THE INVENTION

1. Field of the Invention

The present invention relates to a portable inhaler by means of which a user can inhale medicine.

2. Description of the Related Art

Inhalers designed to eject micro-droplets of medicine into an air flow being breathed in by a user by way of a mouthpiece (inhalation piece) on the basis of the principle of ink-jet systems so as to allow the user to inhale medicine have been developed (see Japanese Patent Applications Laid-Open No. 2004-290593 and No. 2004-283245). Such inhalers have an advantage that a predetermined dose of medicine can be accurately atomized as uniform droplets.

The ejection head for ejecting medicine to be inhaled by a user indispensably requires an element for generating ejection energy and electric power needs to be supplied to the ejection head. Generally, a medicine cartridge is formed by integrally combining an electrical connection section for supplying electric power from a power source arranged in an inhaler body and an ejection head. Such a medicine cartridge may be so formed as to be removably mountable in an inhaler body.

At least when ejecting medicine, an electric circuit needs to be established to supply electric power to the ejection head. However, in an electrically standby status where an electric circuit is established although the inhaler is not in use, medicine can be ejected at an unintended timing in an unexpected situation by an erroneous operation that can take place automatically or by human error.

A scheme for capping the needle of an electric injector when the electric injector is not in use so as to intercept the electrical connection of the injector in order to prevent medicine from being inadvertently ejected is known (see Japanese Patent Application Laid-Open No. H04-312469).

A mouthpiece as described in Japanese Patent Applications Laid-Open No. 2004-290593 or No. 2004-283245 can be so formed as to be removably mountable in an inhaler body. Since the user touches the mouthpiece with his or her mouth, the mouthpiece needs to be cleaned periodically and sanitarily controlled. A removably mountable mouthpiece can be serviced with ease from a sanitary point of view.

The amount of medicine ejected from an inhaler is equal to the dose of medicine to be administered to a user so that it is important to control the amount of medicine to be ejected from an inhaler if compared with an ink-jet recording apparatus particularly when the medicine is costly because the medicine should not be wasted by any means. Therefore, the ejection head of an inhaler is desirably electrically energized only when the inhaler ejects medicine. However, such an inhaler has not been provided to date. With the arrangement of using a cap to intercept the electrical connection when an injector is not in use as described in Japanese Patent Application Laid-Open No. H04-312469, the electrical connection is restored once the cap is taken off so that the injector can be inadvertently operated. In other words, the inhaler cannot break the electrical connection perfectly when the inhaler is not in use.

SUMMARY OF THE INVENTION

In view of the above-identified circumstances, the object of the present invention is to provide an inhaler that can be operated by a user with ease and the ejection head is reliably electrically energized only when the inhaler is operated.

According to the present invention, the above object is achieved by providing an inhaler for allowing a user to inhale medicine ejected from the inhaler by way of an inhalation piece, the inhaler including: a medicine cartridge having an ejection head and a first electrical connection section for supplying the ejection head with electric power necessary for ejecting medicine; an inhaler body having a medicine cartridge mounting section; and an inhalation piece, wherein the inhaler is so constructed that an electric circuit for supplying the ejection head with electric power necessary for ejecting medicine by way of the first electrical connection section is made operable by fixing the inhalation piece on the inhaler body.

Thus, in an inhaler according to the present invention, the ejection head is made to be able to be electrically energized by rigidly securing the inhalation piece to the inhaler body so that medicine is never ejected by error in a state where the inhalation piece is not mounted. The inhalation piece is more often than not made removably mountable to the inhaler body. Therefore, with an arrangement where the inhalation piece is mounted only when the inhaler is to be operated for use, the ejection head is electrically energized as a result of an operation performed by a user of mounting the inhalation piece in the inhaler body so that the inhaler is prevented from ejecting medicine by error by way of such a simple operation.

Other features and advantages of the present invention will be apparent from the following description taken in conjunction with the accompanying drawings, in which like reference characters designate the same of similar parts throughout the figures thereof.

BRIEF DESCRIPTION OF THE DRAWINGS

FIGS. 3A, 3B, 3C and 3D schematically illustrate the cartridge of the inhaler of FIG. 1.

FIGS. 4A and 4B are schematic external views of the cartridge of the inhaler of FIG. 1.

DESCRIPTION OF THE EMBODIMENTS

Preferred embodiments of the present invention will now be described in detail in accordance with the accompanying drawings.

The same components of the embodiments are denoted respectively by the same reference numbers in principle and will not be described repeatedly.

First Embodiment

Figure 1:
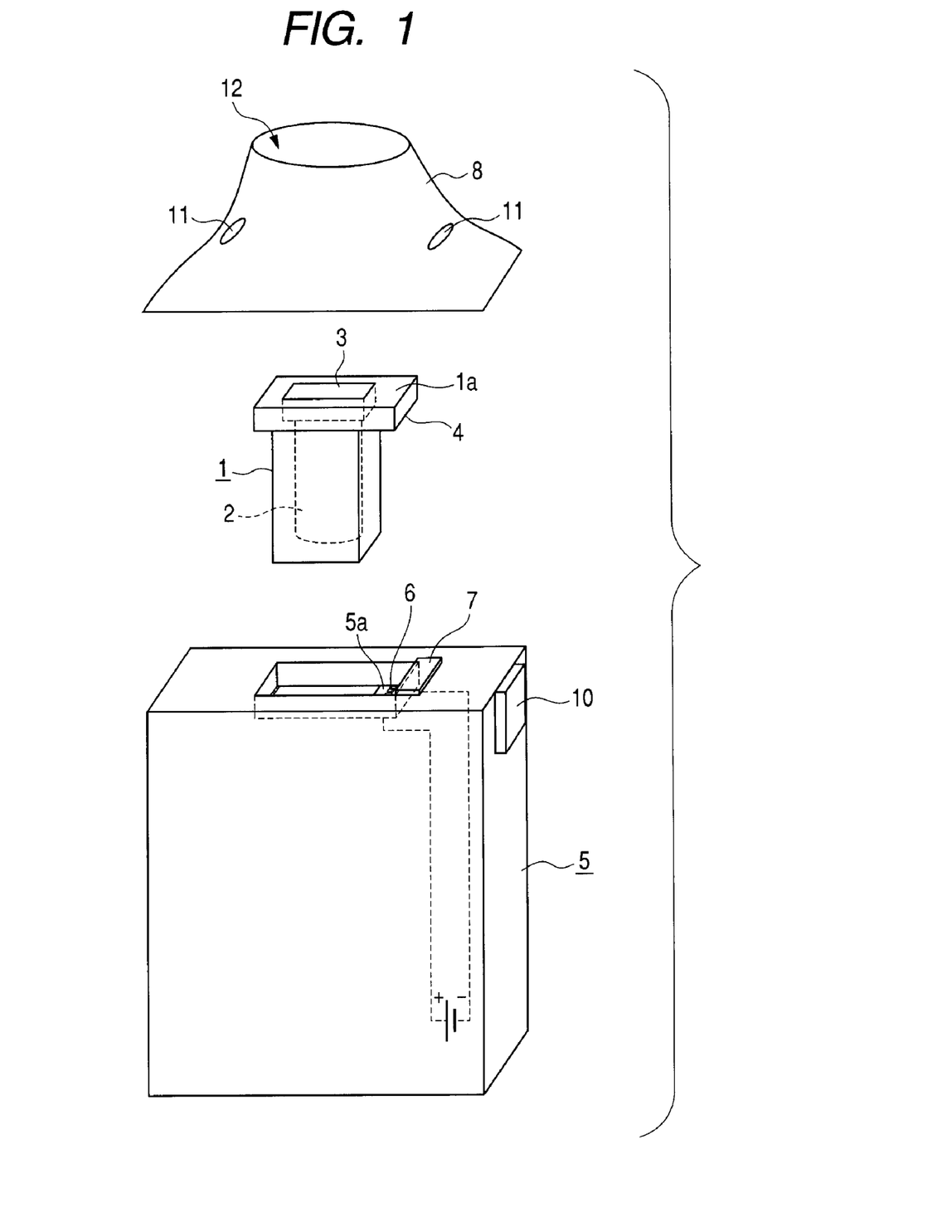
FIG. 1 is an exploded schematic perspective view of the inhaler of Embodiment 1.
Figure 2:
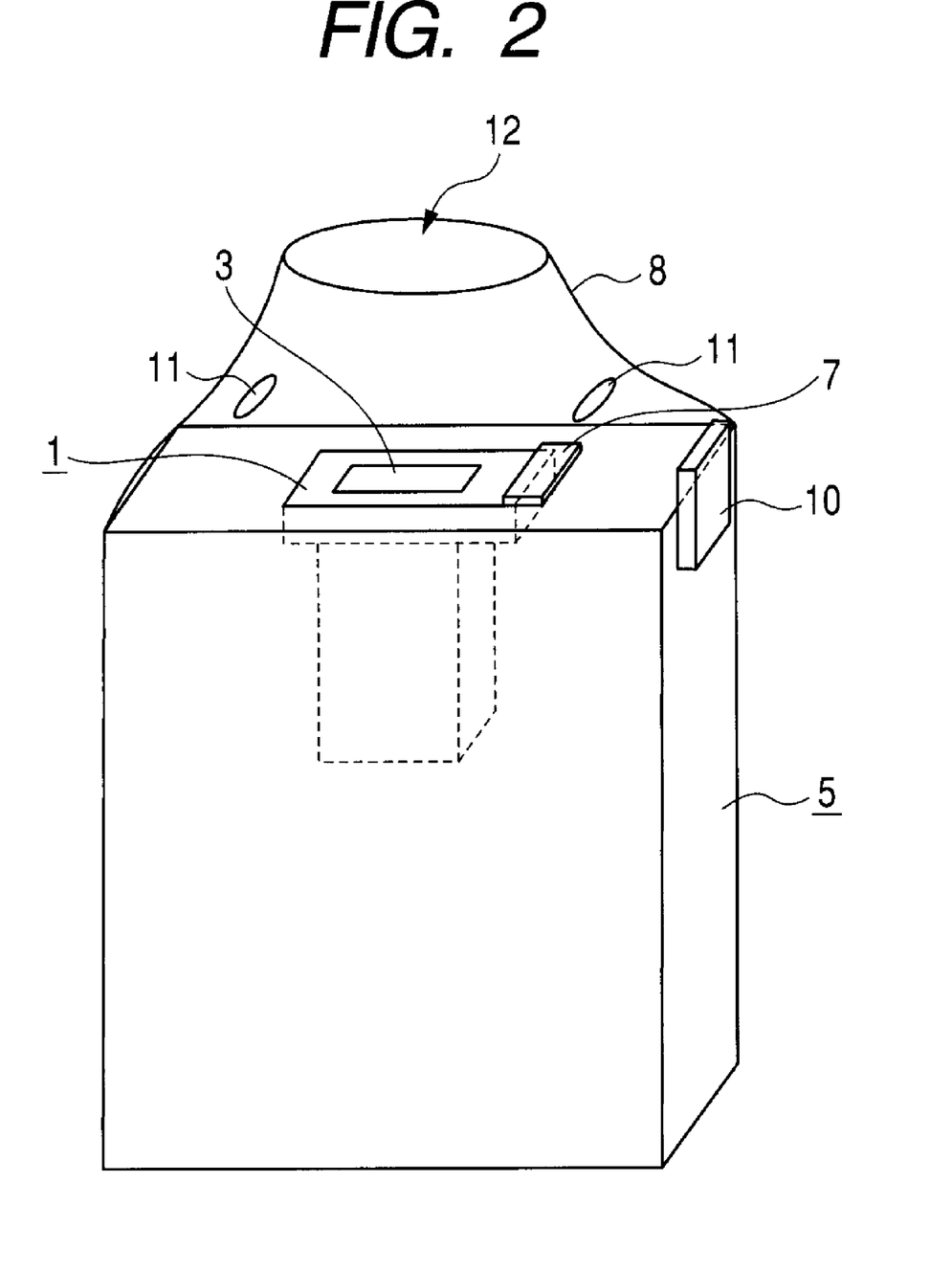
FIG. 2 is a schematic perspective view of the inhaler of FIG. 1 in an assembled state with a see-through view of the inhalation piece thereof.

FIG. 1 is an exploded schematic perspective view of the inhaler of Embodiment 1 and FIG. 2 is a schematic perspective view of the inhaler of FIG. 1 in an assembled state. Referring to FIGS. 1 and 2, a medicine cartridge 1 has at least an ejection head 3 for ejecting medicine and a first electrical connection section 4 for supplying the ejection head 3 with electric power necessary for ejecting medicine. Wiring (not illustrated) extends from the first electrical connection section 4 to the ejection energy generating element of the ejection head 3. In this embodiment, a medicine tank (reservoir) 2 for containing medicine to be ejected is integrated with the cartridge. The inhaler body 5 has a cartridge mounting section 5a for receiving the medicine cartridge and securely holding the medicine cartridge. Additionally, the inhaler has an inhalation piece 8 that is to be put to the user's mouth or nose in order for the user to inhale the medicine ejected from the ejection head 3. The inhalation piece 8 has an air intake port 11 through which the inside of the inhalation piece 8 communicates with the outside thereof so as to produce an air flow, by means of which the user inhales medicine.

In an inhaler according to the present invention, an electric circuit for supplying the ejection head 3 with electric power by way of the first electrical connection section 4 becomes operational as the inhalation piece 8 is rigidly secured to the inhaler body 5. In this embodiment, the inhaler body 5 is provided with a second electrical connection section 6 that can be electrically connected to the first electrical connection section 4. The first electrical connection section 4 and the second electrical connection section 6 contact each other to allow an electric current to flow through them only when the inhalation piece 8 is mounted on and rigidly secured to the inhaler body 5 by means of an inhalation piece fixing member 10. Then, electric power can be supplied from the inhaler to the ejection head 3. The inhalation piece is an indispensable component of the inhaler and preferably removably mountable to the inhaler from a sanitary point of view. Therefore, it is highly advantageous to use the inhalation piece as trigger for establishing electrical connection according to the present invention.

For the purpose of the present invention, "electric power" may refer to DC, AC or a pulse-shaped drive signal for driving the ejection head, a DC voltage or a constant current for driving the ejection head.

The inhaler body 5 may have a cartridge fixing member 7 that is separate from the inhalation piece 8. Any generally available means may be used for the cartridge fixing member 7 so long as the cartridge fixing member can reliably secure the cartridge 1 to the inhaler body 5. For example, the generally available means may be a physical means such as a pawl or a stopper, a means that can bond the cartridge 1 to the inhaler body 5 with ease or a non-contact means such as magnetic power.

When a separate fixing member is not employed, the cartridge 1 is preferably rigidly secured to the inhaler as the inhalation piece 8 is rigidly secured to the inhaler body.

An air flow is generated and directed from the air intake ports 11 toward an inhalation opening (suction port) 12 as the user holds the inhalation piece 8 in his or her mouth or contacts the inhalation opening 12 in some other way and breathes in. Then, as medicine is ejected into the airflow duct, medicine is carried toward the inhalation piece 8 by the air flow that operates as medicine carrier and administered to the user. The inhalation opening 12 may be so profiled that the user inhales medicine through the mouth or the nose.

The inhalation piece may have any appropriate profile. More specifically, the inhalation piece may be box-shaped or alternatively the inhalation piece may have a curved profile. Preferably, however, the part of the inhalation piece that is brought into contact with the user is designed on the basis of human engineering and the remaining part is designed so as not to influence the air flow and the mist.

The inhaler body may be provided with a CPU (control section) that controls the operation of the entire inhaler including the operation of driving the ejection head. Furthermore, the inhaler body may be provided with a sensor for detecting an air flow and also the difference between the atmospheric pressure and the air pressure that is produced in the inside of the airflow duct as the user breathes and the inhaler may be so designed as to transmit a drive signal representing the air flow and the pressure difference that are detected by the sensor from the control section to the ejection head so as to synchronously start ejecting medicine according to the signal. Still additionally, the inhaler body may also be provided with a display section for displaying information that makes the user visually recognize the operation he or she is doing on the inhaler, the condition of the current ejection of medicine and so on.

The inhaler is provided with a power switch (not illustrated) and the system of the inhaler is made ready for various operations according to an operation signal transmitted from the power switch. As for power supply, a battery is arranged in the inhaler body and power is supplied from the battery to various relevant components by way of electric wiring in order to operate the ejection head and the system. Any type of battery may be employed for the purpose of the present invention so long as the battery can supply power at a desired rate with a desired level of voltage and a desired level of current. The inhaler may be provided with a power supply port (not illustrated) so that power may be supplied to the inhaler from an external power source. In this embodiment, wiring extends from the power source arranged in the inhaler body 5 to the second electrical connection section 6 so that electric power can be supplied to the ejection head as the medicine cartridge 1 is mounted on and rigidly secured to the inhaler body 5.

(Medicine Cartridge)

Figure 3A:
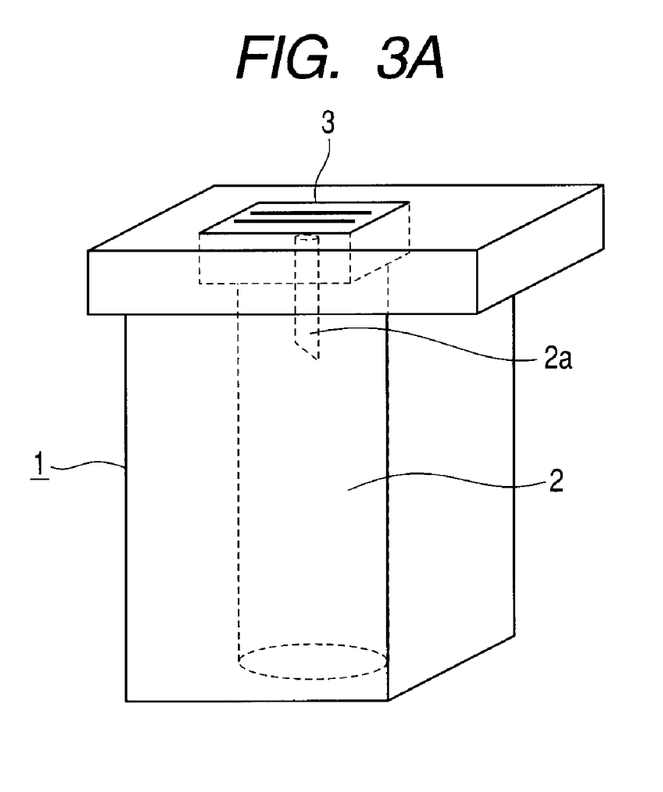
FIG. 3A is a schematic perspective view of the cartridge, illustrating the internal structure thereof with broken lines.

FIGS. 3A through 3D, 4A, 4B, 5A and 5B illustrate preferred medicine cartridges that can be used for the first embodiment. As illustrated in FIG. 3A, a medicine flow path is formed in the cartridge 1 between the ejection head 3 having a nozzle array for ejecting medicine and the medicine tank 2 by means of a communication needle 2a so that medicine is supplied from the medicine tank 2 to the ejection head 3.

Figure 4A:
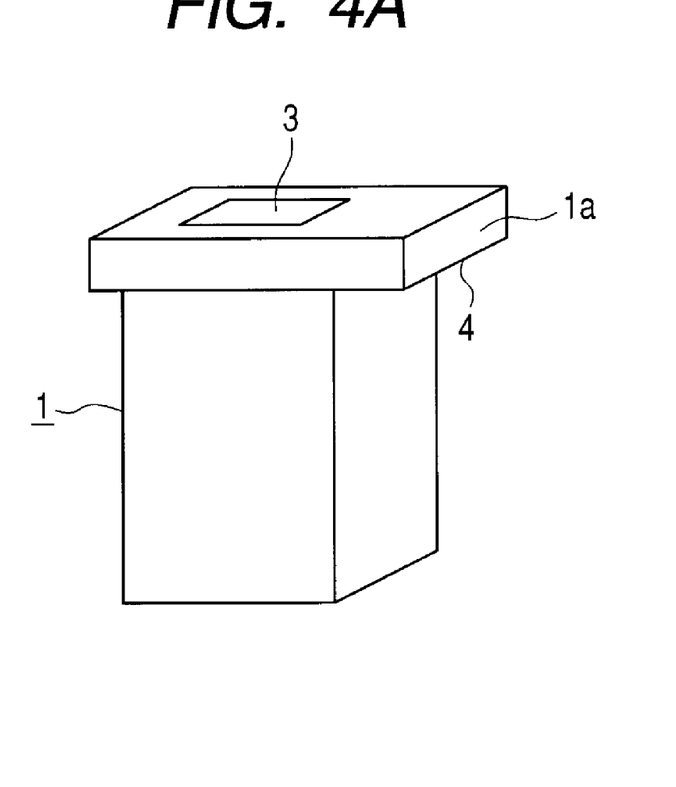
FIG. 4A is a schematic perspective view of the cartridge.
Figure 4B:
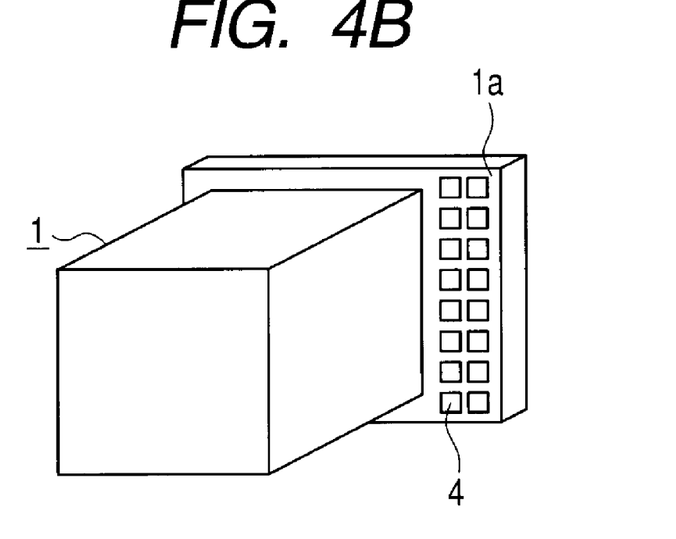
FIG. 4B is a schematic perspective view of the cartridge turned to lie on one of the lateral sides thereof.

As illustrated in FIGS. 4A and 4B, the first electrical connection section 4 for supplying electric power to the ejection head 3 is arranged at the junction forming section 1a that projects from the lateral sides of the cartridge 1. After the cartridge 1 is put into the inhaler body 5, the inhalation piece 8 is rigidly secured to the inhaler body 5 by means of the inhalation piece fixing member 10 and the first electrical connection section 4 is forced to abut the second electrical connection section 6 arranged at the cartridge mounting section 5a of the inhaler body 5 so as to establish electrical connection between the cartridge 1 and the inhaler body 5. For the purpose of the present invention, the "junction forming section" arranged at the cartridge refers to an appropriate part of the surface of the cartridge 1 that is brought into contact with the inhaler body 5 when the cartridge 1 is mounted on the inhaler body 5. On the other hand, the "cartridge mounting section" of the inhaler body 5 refers to the part thereof that is brought into contact with the cartridge 1 when the cartridge 1 is mounted on the inhaler body 5. For the purpose of the present invention, the first electrical connection section 4 is arranged at the junction forming section of the cartridge, while the second electrical connection section 6 is arranged at the cartridge mounting section of the inhaler body. The electrical connection sections 4 and 6 are arranged respectively at the junction forming section and at the cartridge mounting section so as to be placed vis-à-vis when the cartridge 1 is mounted on the inhaler body 5.

Thus, since the electrical connection sections 4 and 6 are so formed as to abut and contact each other in the direction in which the cartridge 1 is mounted on the inhaler body 5, the electrical connection section 4 and 6 are hardly worn and degraded and hence connection failure and other troubles are minimized if the cartridge 1 is removably mounted on the inhaler body 5 frequently. The electrical connection sections 4 and 6 can be formed by using any material so long as a desired level of electric conductivity is realized. The electrical connection sections 4 and 6 may be provided with projections and recesses. For the purpose of the present invention, the direction in which the cartridge 1 is mounted on the inhaler body 5 refers to the direction in which the cartridge 1 moves relative to the inhaler body 5 when the cartridge 1 is mounted. It is the longitudinal direction in FIG. 1.

The electrical connection section of the cartridge is preferably arranged at a position close to the ejection head. A long wiring distance is disadvantageously required when the electrical connection section of the cartridge is separated from the ejection head by a large distance.

Preferably, the electrical connection section of the cartridge is formed by a plurality of terminals, all of which terminals are arranged on a same plane. Preferably, the plane where all the terminals of the electrical connection section are arranged is perpendicular to the direction in which the cartridge is removably mounted on the inhaler body.

Preferably, a projecting section is arranged to project from the lateral sides of the cartridge on the plane where the ejection head is placed and the projecting section is provided with the electrical connection section. With this arrangement, both the cartridge and the inhaler body can be made to show a simple structure and the electrical connection sections can be arranged at respective positions that are visually highly recognizable to the user so that the reliability is improved and the user can make sure with ease that electrical connection is established between the cartridge and the inhaler body and the cartridge is mounted in position. Preferably, the terminals (contact pins) of the electrical connection section are arranged on the flat projecting section that projects from the cartridge in directions perpendicular to the direction in which the cartridge is put into the inhaler body as seen from FIGS. 3A through 3D. Preferably, the terminals are arranged on the rear side of the projecting section that is opposite to the side where the ejection head 3 is formed.

Figure 3B:
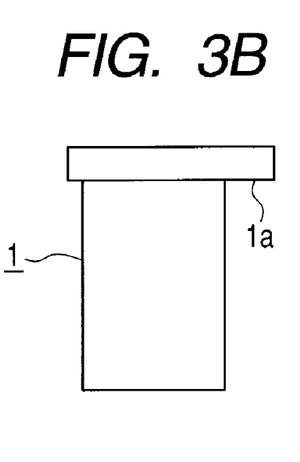
FIG. 3B is a schematic lateral view of the cartridge.
Figure 3C:
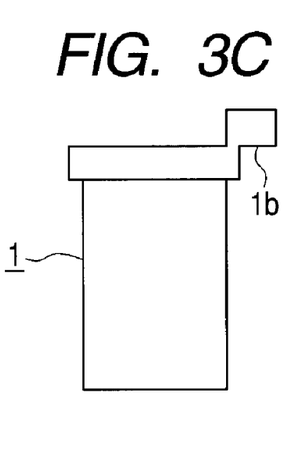
FIGS. 3C and 3D are schematic lateral views of two cartridges formed by modifying the cartridge of FIG. 3B.
Figure 3D:
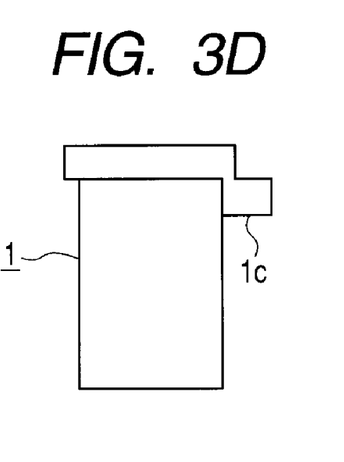

As illustrated in FIG. 3B, the projection section of the cartridge 1 having the junction forming section 1*a* where the electrical connection section 4 is arranged projects from the lateral sides of the main body of the cartridge 1. The projecting section may show a profile selected from a variety of different possible profiles so long as the projection section projects in the vicinity of the ejection head 3. For example, FIG. 3C illustrates an instance where a junction forming section 1*b* is formed on the bottom surface of the part of a projecting section whose top surface is displaced toward the inhalation piece from the plane of the cartridge 1 where the ejection head is arranged. FIG. 3D illustrates an instance where a junction forming section 1*c* is formed on the bottom surface of the part of a projecting section whose top surface is displaced conversely toward the inside of the inhaler body 5.

The instance where a junction forming section 1*b* is formed on the bottom surface of the part of a projecting section whose top surface is displaced toward the inhalation piece from the plane of the cartridge 1 where the ejection head is arranged provides an advantage that the user can visually recognize the established electrical connection very easily, whereas the instance where a junction forming section 1*c* is formed on the bottom surface of the part of a projecting section whose top surface is displaced conversely toward the inside of the inhaler body 5 provides an advantage that the cartridge can be secured to the inhaler body very reliably.

Figure 5A:
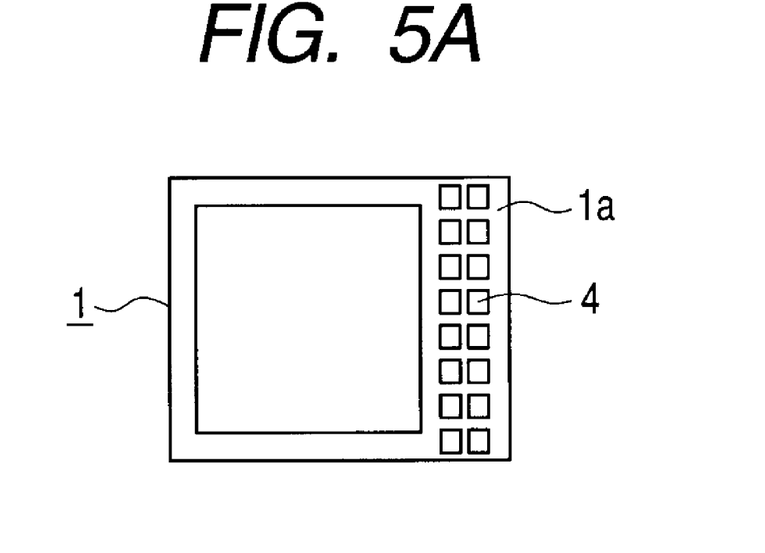
FIGS. 5A and 5B are a schematic view of the electrical connection section of the cartridge and a schematic view of the electrical connection section of the inhaler body.
Figure 5B:
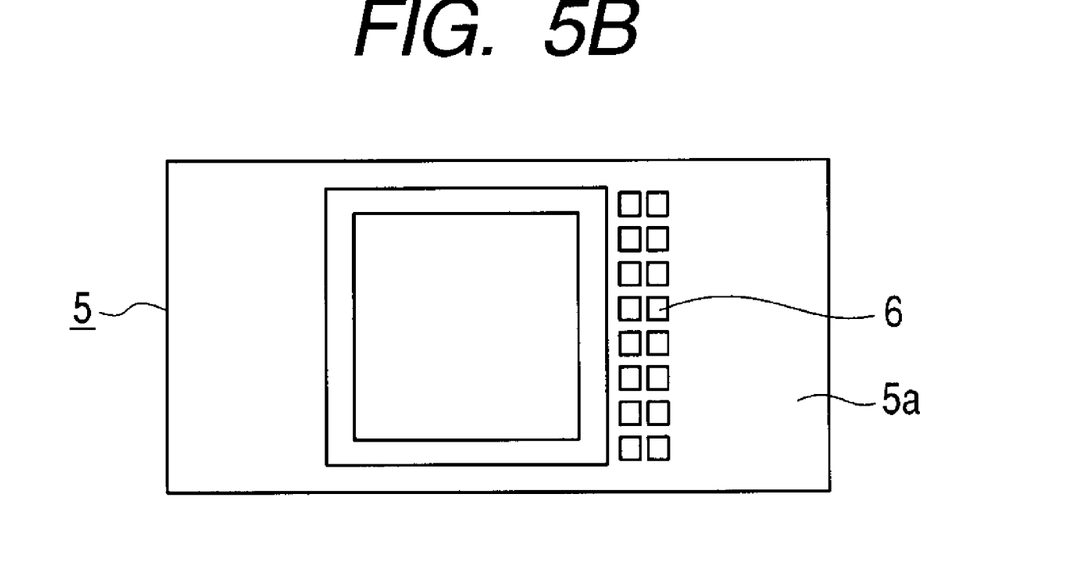

As illustrated in FIGS. 5A and 5B, the electrical connection section 4 of the cartridge and the electrical connection section 6 of the inhaler body that are arranged vis-à-vis and contact each other are arranged at suitable respective positions in a suitable manner according to the projecting profile of the junction forming section 1*a* of the cartridge 1.

The reliability of the operation of the inhaler is improved by the scheme that does not electrically energize the inhaler when the cartridge 1 is put into the inhaler body 5 but electrically energizes the inhaler only when the inhalation piece 8 is rigidly secured to the inhaler body by the cartridge fixing member 7. This scheme can be realized by arranging a restitutive member (not illustrated) such as a spring in the space in the inhaler body for receiving a cartridge 1. With such an arrangement, the cartridge 1 is not electrically energized when the cartridge 1 is put into the inhaler body 5 but becomes electrically energized only when the cartridge 1 is forced into the space against the restitutive member by the inhalation piece 8.

In an inhaler according to the present invention, the ejection head 3 has an appropriate ejection energy generating element. The ejection energy generating element may be an electrothermal transducer that applies thermal energy to medicine or an electromechanical transducer that applies mechanical energy to medicine. A thermal jet system for applying thermal energy to medicine by means of an electrothermal transducer and causing the medicine to be ejected from an ejection port or a system for using an electromechanical transducer (e.g., a piezoelectric element) to apply mechanical energy to medicine and causing the medicine to be ejected from the ejection port under the vibration pressure of the electromechanical transducer may be used for the purpose of the present invention. The ejection system to be used for an inhaler according to the present invention may be selected depending on the type of medicine.

When a thermal jet system is employed, individual liquid ejection units can be made to show a high level of dimensional accuracy and reproducibility in terms of the bore of the ejection port, the calories of the thermal pulse to be used for ejecting medicine, the size of the electrothermal transducer, which may typically be a micro-heater, etc. Therefore, the distribution of liquid droplets can be confined to a small and narrow area. Additionally, a thermal jet type ejection head can be manufactured at low cost and hence can find applications in small apparatus that require the ejection head to be replaced frequently. Thus, a thermal jet type inhaler is preferable particularly when the medicine inhaler is required to be portable and convenient for use.

For the purpose of the present invention, ingredients contained in the medicine include not only medicinal compounds that provide pharmaceutical and physiological effects but also tasty and fragrant ingredients, aromatics, dyes and pigments. Additionally, for the purpose of the present invention, medicine may be liquid or powder.

For the purpose of the present invention, liquid medicine is not limited to the medicine including only liquid components and may include solid components in the liquid. Liquid medicine may contain any additive (s). As for the state of the medicine contained in the liquid, the medicine may be dissolved, dispersed, emulsified, suspended or slurried. Preferably, it may uniformly exist in liquid.

When medicinal liquid is employed as medicine, the liquid major medium is preferably water or an organic compound. The liquid major medium is more preferably water from the viewpoint that the medicinal liquid is administered to a living body.

An inhaler according to the present invention can find various applications. Medicine can be administered by means of an inhaler according to the present invention by way of the mouth or the nose of a user having a locally diseased respiratory organ or a diseased circulatory system of the entire body. Additionally, a particular site in the user's body can be targeted. Respiratory diseases that can be treated by means of an inhaler according to the present invention include asthma and chronic obstructive lung diseases, whereas diseases of the circulatory system of the entire body include diabetes mellitus.

Second Embodiment

Figure 6:
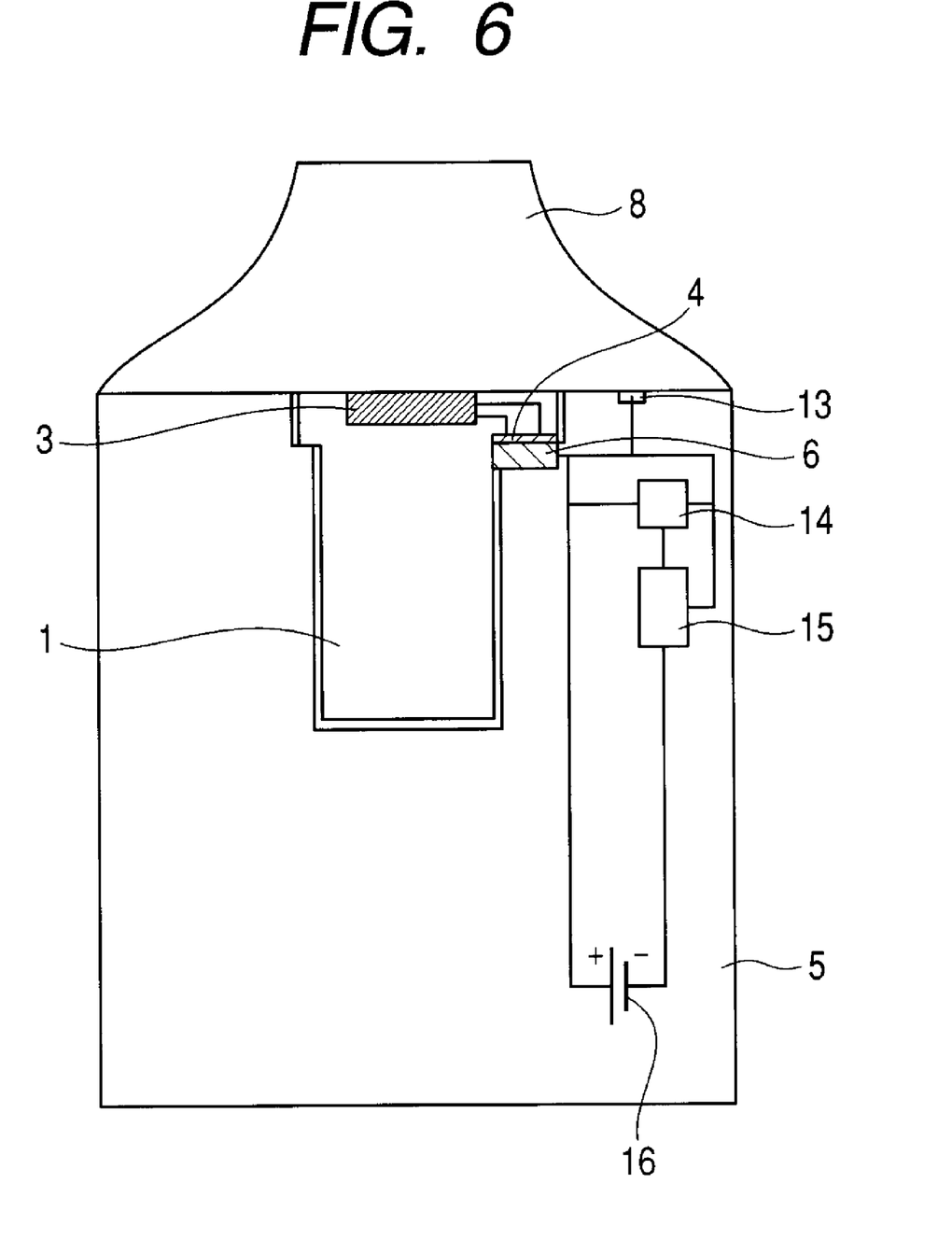
FIG. 6 is a schematic cross-sectional view of the inhaler of Embodiment 2 of the present invention.

FIG. 6 is a schematic cross sectional view of the inhaler of Embodiment 2 of the present invention. This embodiment has a sensor 13 for detecting that the inhalation piece 8 is rigidly secured to the inhaler body 5. This embodiment additionally has a switching circuit that is a switching means for making the electric circuit operational in response to an output of the sensor 13 indicating that the inhalation piece 8 is rigidly secured to the inhaler body.

A switching circuit may be arranged between the first electrical connection section and the last electrical connection section of the electric circuit formed in the embodiment in order to establish electrical connection. The electrical connection section 4 of the ejection head 3 has a plurality of terminals and is a multi-wire site in the entire circuit. A switching circuit may be arranged to reduce the multi-wire site and simplify the wiring. Such a switching circuit is preferably arranged near the electrical connection section of the cartridge from the viewpoint of electric wiring relative to the electric wiring section. The switching circuit may be in the inhaler body or in the inhalation piece.

The first electrical connection section 4 of the cartridge 1 and the second electrical connection section 6 at the side the inhaler are apparently already brought into contact with and connected to each other in a state where the cartridge 1 is mounted on the inhaler body but the circuit configuration can be modified by means of the switching circuit 14 and the control section 15 of the circuit.

After the cartridge 1 is mounted on the inhaler, the inhalation piece 8 is fitted to the top surface of the inhalation head 3 in the cartridge. The ejection head 3 is electrically connected to the first electrical connection section 4 by head wiring. The second electrical connection section 6 is arranged on the cartridge mounting section 5a of the inhaler and the ejection head 3 is electrically connected to the inhaler as the first electrical connection section 4 is brought into contact with the second electrical connection section 6. The inhaler has a power source 16 and electric power is supplied from the power source 16 to the ejection head 3. The power source 16 may be a battery or a connector for connecting the inhaler to an external power source.

When the inhalation piece 8 is detected to have been rigidly secured to the inhaler body from the output of the sensor 13, the control section 15 switches the switching circuit 14 so as to establish an electric circuit for supplying power to the ejection head and make the inhaler operational. Conversely, so long as the inhalation piece is not rigidly secured to the inhaler body, the control section 15 holds the switching circuit 14 to a state of not establishing any such electric circuit.

Third Embodiment

Figure 7:
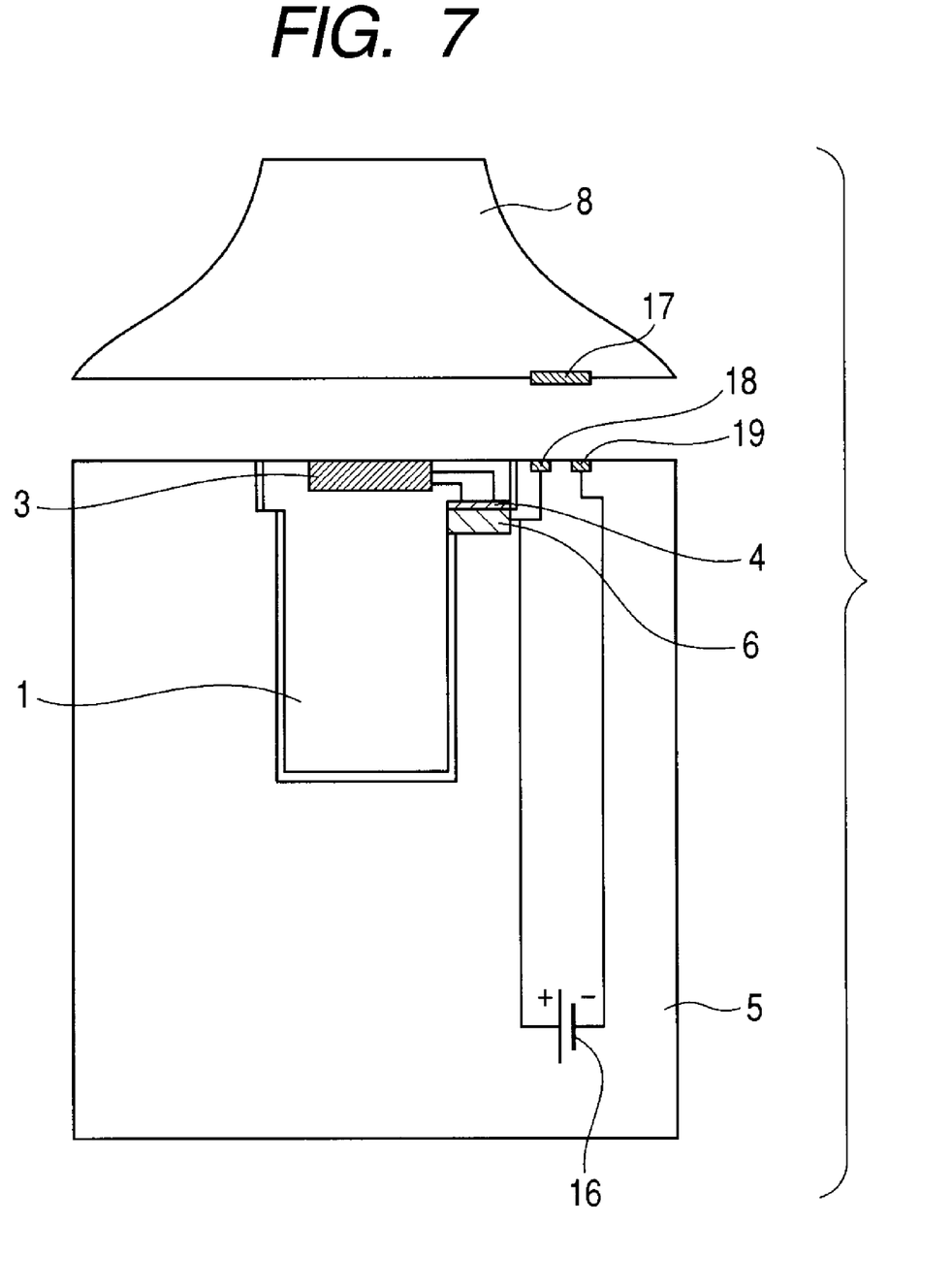
FIG. 7 is a schematic cross sectional view of the inhaler of Embodiment 3 of the present invention.

FIG. 7 is a schematic cross sectional view of the inhaler of Embodiment 3 of the present invention. In this embodiment, the electric circuit for supplying electric power to the ejection head is at least partly arranged in the inhalation piece 8. FIG. 7 illustrates a state where the inhalation piece 8 is not mounted on and rigidly secured to the inhaler body 5 yet.

As illustrated in FIG. 7, a third electrical connection section 17 that operates as part of the electric circuit is arranged on the surface of the inhalation piece 8 to be put on the inhaler. A fourth electrical connection section 18 and a fifth electrical connection section 19 are arranged on the surface of the inhaler for receiving the inhalation piece 8 at respective positions located vis-à-vis the third electrical connection section 17 and separated from each other. The fifth electrical connection section 19 is connected to a power source 16 and the fourth electrical connection section 18 is connected to the second electrical connection section 6 arranged at the cartridge mounting section. The arrangement and the configuration of the cartridge are the same as those of the preceding embodiments. As the inhalation piece 8 is mounted on the inhaler, the fourth electrical connection section 18 and the fifth electrical connection section 19 that are separated from each other are electrically connected to each other by way of the third electrical connection section 17 to establish an electric circuit for supplying electric power to the ejection head 3.

The third electrical connection section 17 is not subjected to any limitations so long as the third electrical connection section 17 is formed as an electrically conducting member. For instance, the third electrical connection section 17 may be formed by using metal. Furthermore, the third electrical connection section 17 may be formed as a single terminal or as an electrical connection section having terminals, the number of which is the same as that of the plurality of electrical connection terminals provided for the ejection head. A switching circuit may be arranged between the first electrical connection section and the last electrical connection section of the electric circuit formed in the embodiment in order to establish electrical connection. The electrical connection section 4 of the ejection head 3 has a plurality of terminals and is a multi-wire site in the entire circuit. A switching circuit may be arranged to reduce the multi-wire site and simplify the wiring. Such a switching circuit is preferably arranged near the electrical connection section of the cartridge from the viewpoint of electric wiring relative to the electric wiring section. The switching circuit may be in the inhaler body or in the inhalation piece.

Furthermore, a general purpose fixing member may be employed for rigidly securing the inhalation piece 8 to the inhaler and an electrically conducting member may be arranged there.

Fourth Embodiment

Figure 8:
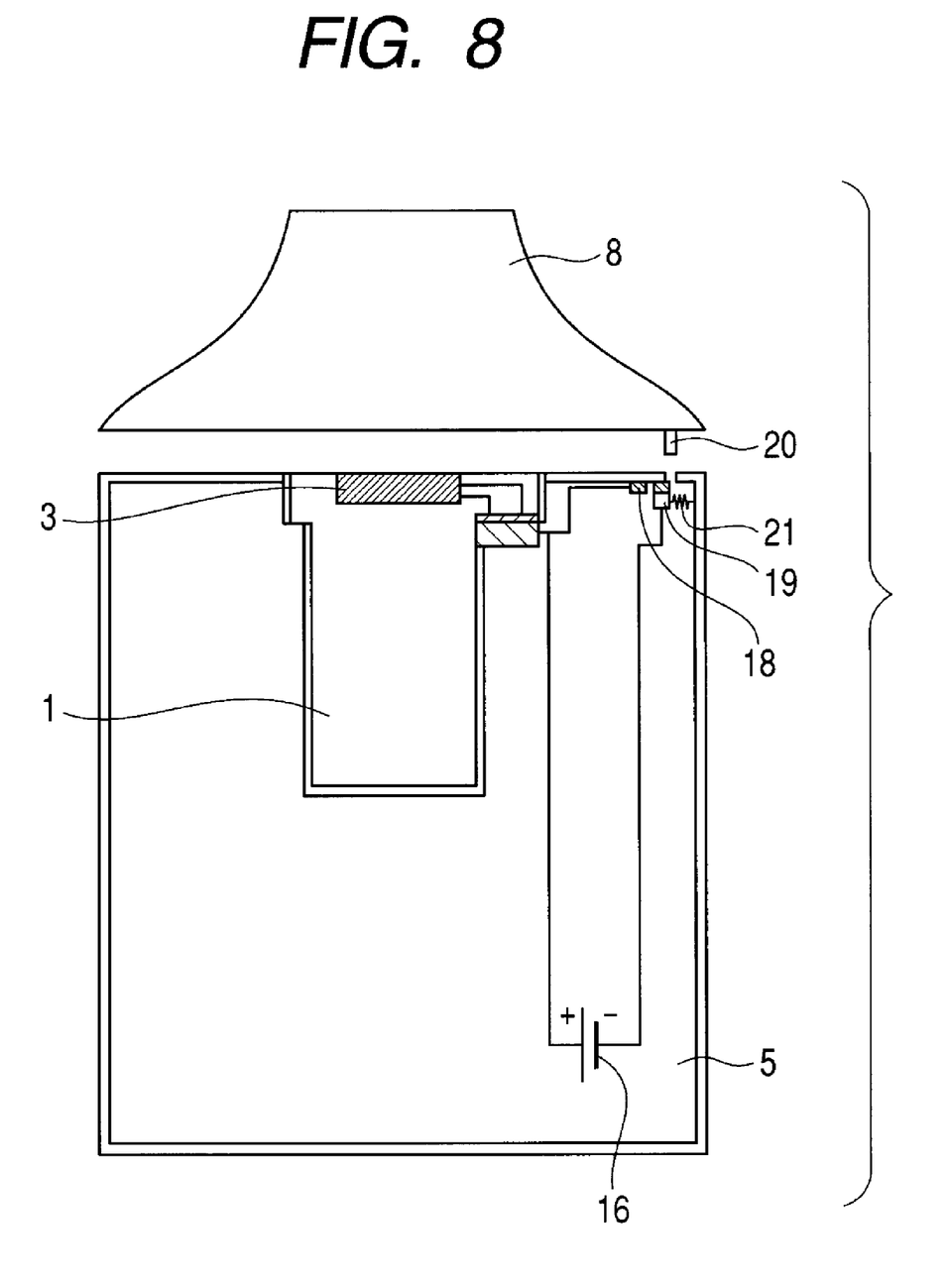
FIG. 8 is a schematic cross sectional view of the inhaler of Embodiment 4 of the present invention.

FIG. 8 is a schematic cross sectional view of the inhaler of Embodiment 4 of the present invention. FIG. 8 illustrates a state before the inhalation piece 8 is mounted on and rigidly secured to the inhaler body 5. This embodiment has a pawl member 20 having a profile adapted to be inserted into an opening formed at the inhaler. The pawl member 20 operates as a fixing member for rigidly securing the inhalation piece 8 to the inhaler body. A fifth electrical connection section 19 is arranged near the opening and connected flexibly to the inhaler body by means of a spring 21. As the pawl member 20 is put into the opening of the inhaler and the inhalation piece 8 is rigidly secured to the inhaler, the pawl member 20 pushes down the fifth electrical connection section 19 and the moved fifth electrical connection section 19 contacts the fourth electrical connection section 18. Then, as a result, the electric circuit for supplying electric power to the ejection head 3 becomes operational. This embodiment operates highly reliably because the inhalation piece is perfectly rigidly secured to the inhaler body by means of an inhalation piece fixing member to establish an electric circuit.

Alternatively an electrically conducting member that forms part of the electric circuit may be arranged at the pawl member 20 and inserted into the opening to make the electrically conducting member contact the fourth electrical connection section 18 and the fifth electrical connection section 19 and establish an electric circuit.

Fifth Embodiment

Figure 9:
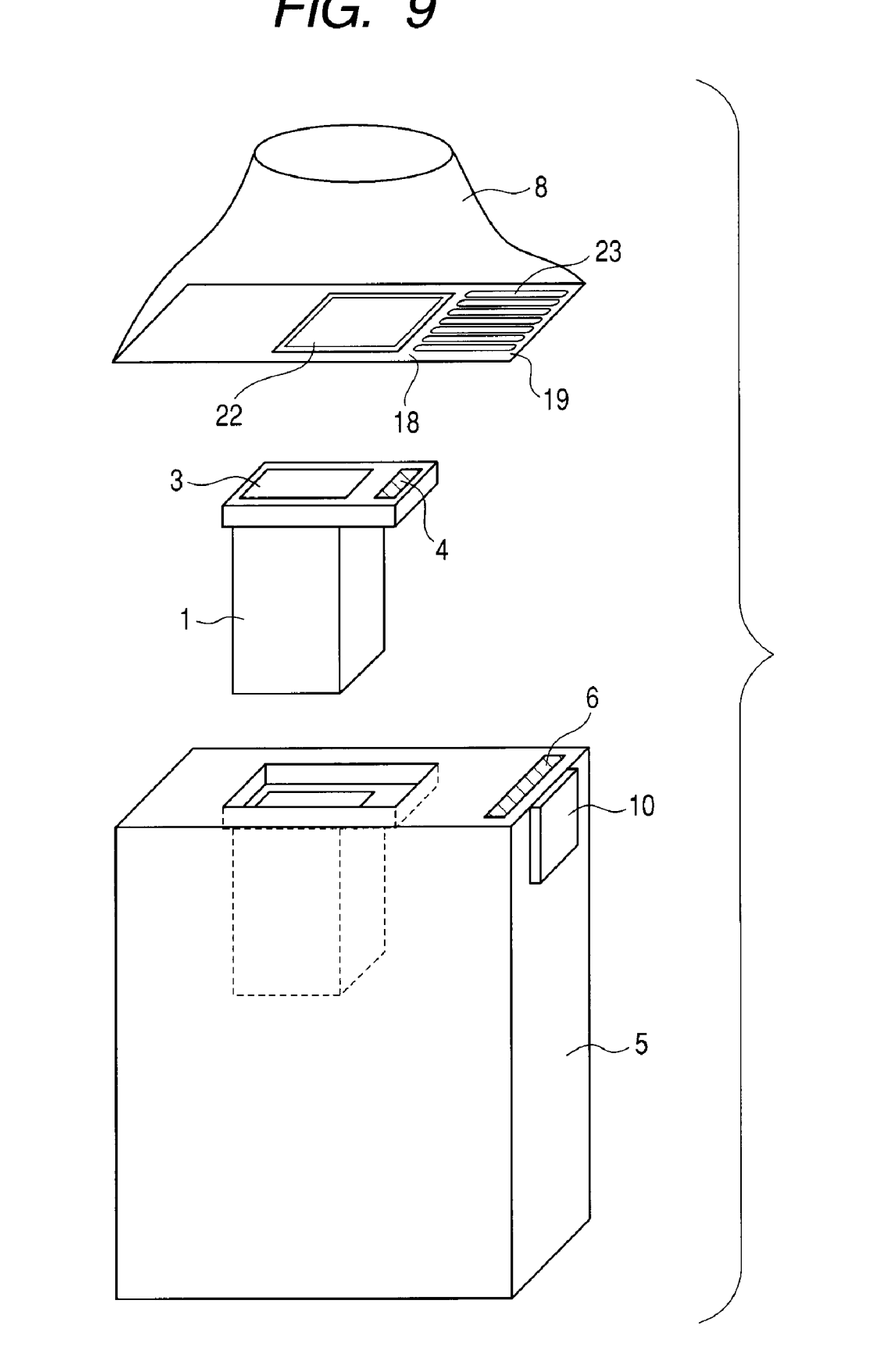
FIG. 9 is an exploded schematic cross sectional view of the inhaler of Embodiment 5 of the present invention.

FIG. 9 is an exploded schematic cross sectional view of the inhaler of Embodiment 5 of the present invention. FIG. 9 illustrates a state before the inhalation piece 8 and the medicine cartridge 1 are mounted on and rigidly secured to the inhaler body 5. The inhalation piece 8 of this embodiment is provided with two electrical connection sections.

An electric wiring 23 is arranged adjacently relative to the atomization port 22 of the inhalation piece 8 and a fourth electrical connection section 18 and a fifth electrical connection section 19 are arranged at the opposite ends of the electric wiring 23, while a second electrical connection section 6 is arranged at part of the surface of the inhaler body 5 for receiving the inhalation piece 1 that is located vis-à-vis the fifth electrical connection section 19. All the first, second, fourth and fifth electrical connection sections come to operate for conducting electricity as the inhalation piece 8 is mounted on and rigidly secured to the inhaler body 5. An insulation member may be provided to cover the electrical connection sections in order to protect the electrical connection sections against liquid that may come from the surrounding. While the insulation member may be made of any appropriate material and have any appropriate profile, the insulation member is preferably formed by using a resilient member in order to provide a hermetically sealing effect. The fixing member 10 of this embodiment is driven to slide and rigidly secured in position in order to mount the inhalation piece 8 on the inhaler body 5 and rigidly secure the former to the latter. The fixing member 10 may be a part of the circuit.

Since the electric wiring 23 is arranged by using a plurality of wires in FIG. 9, the fourth electrical connection section 19 and the matching second electrical connection section 6 are made to have a plurality of terminals correspondingly. Alternatively, however, a switching circuit may be arranged at the electric wiring 23 and the fourth and second electrical connection sections may be made to have a single terminal.

It may alternatively be so arranged that the inhalation piece 8 is connected to the inhaler body 5 at an end thereof by way of a rotary section and the inhalation piece 8 is rigidly secured to the inhaler body 5 as the inhalation piece 8 is turned relative to the inhaler body 5.

Sixth Embodiment

The sixth embodiment of the present invention has an intercepting means for intercepting the electric circuit thereof in a state where the inhalation piece 8 is rigidly secured to the inhaler body. With this arrangement, the electric circuit for supplying electric power to the ejection head 3 can be intercepted and made inoperative when the inhaler is not in use and stored without taking off the inhalation piece 8 in order to prevent medicine from being inadvertently ejected when the inhaler is not in use.

More specifically, referring to FIGS. 6 through 8, the second electrical connection section 6 at the side of the inhaler body 5 may be made movable. For example, a fixing member may be arranged under the second electrical connection section 6 and made to extend to the outer surface of the inhaler body 5. As the user pulls the fixing member outwardly, the second electrical connection member 6 is moved away from the fixing member and electrically disconnected from the first electrical connection section 4 so as to bring the inhaler in an electrically insulated state and intercept the entire electric circuit of the inhaler.

The present invention is not limited to the above embodiments and various changes and modifications can be made within the spirit and scope of the present invention. Therefore, to apprise the public of the scope of the present invention, the following claims are made.

This application claims the benefit of Japanese Patent Application No. 2008-200942, filed on Aug. 4, 2008, which is hereby incorporated by reference herein in its entirety.

What is claimed is:

1. An inhaler for allowing a user to inhale medicine ejected from the inhaler by way of an inhalation piece, the inhaler comprising:
   a medicine cartridge having an ejection head and a first electrical connection section for supplying the ejection head with electric power necessary for ejecting medicine;
   an inhaler body having a medicine cartridge mounting section for mounting the medicine cartridge; and
   an inhalation piece being separately secured to the inhaler body, wherein,
   the inhaler is so constructed that an electric circuit for supplying the ejection head with electric power necessary for ejecting medicine is made operable by fixing the inhalation piece on the inhaler body.

2. The inhaler according to claim 1, wherein the inhaler body has a second electrical connection section that is electrically connectable to the first electrical connection section, wherein an electrical connection is established between the first electrical connection section and the second electrical connection section as the inhalation piece is fixed to the inhaler body.

3. The inhaler according to claim 1, wherein
   the inhaler has a sensor for detecting that the inhalation piece is fixed to the inhaler body and the electric circuit is adapted to be made operable according to the output of the sensor.

4. The inhaler according to claim 1, wherein
   at least part of the electric circuit is arranged in the inhalation piece.

5. The inhaler according to claim 1, wherein the medicine cartridge is fixed to the inhaler body by fixing the inhalation piece on the inhaler body.

6. The inhaler according to claim 1, wherein the electric circuit is adapted to be intercepted in a state where the inhalation piece is fixed on the inhaler body.

7. The inhaler according to claim 2, wherein the first electrical connection section and the second electrical connection section are held in touch with and connected to each other in the direction in which the medicine cartridge is mounted on the inhaler body.

\* \* \* \* \*